United States Patent [19]
Oliveira et al.

[11] Patent Number: 5,996,584
[45] Date of Patent: Dec. 7, 1999

[54] SEALING STRIP FOR EAR PLUGS AND THE LIKE

[75] Inventors: Robert J. Oliveira, Maplewood; Davis W. Chamberlin, Saint Paul, both of Minn.

[73] Assignee: Hearing Components, Inc., Oakdale, Minn.

[21] Appl. No.: 09/035,115

[22] Filed: Mar. 5, 1998

[51] Int. Cl.$^6$ .................................................. A61F 11/00
[52] U.S. Cl. ........................................... 128/864; 128/865
[58] Field of Search .................... 128/864–868; 181/129, 130

[56] References Cited

U.S. PATENT DOCUMENTS

| | | | |
|---|---|---|---|
| Re. 29,487 | 12/1977 | Gardner, Jr. ............................. | 128/152 |
| 4,338,929 | 7/1982 | Lundin .................................... | 128/864 |
| 4,880,076 | 11/1989 | Ahlberg et al. .......................... | 181/130 |
| 5,002,151 | 3/1991 | Oliveira et al. ........................... | 181/130 |
| 5,153,387 | 10/1992 | Zwislocki et al. ....................... | 181/129 |
| 5,188,123 | 2/1993 | Gardner, Jr. ............................. | 128/864 |
| 5,333,622 | 8/1994 | Casali ...................................... | 128/864 |
| 5,573,015 | 11/1996 | Williams ................................. | 128/864 |
| 5,682,020 | 10/1997 | Oliveira .................................. | 181/130 |

FOREIGN PATENT DOCUMENTS

| | | | |
|---|---|---|---|
| 341238 | 12/1971 | Germany ................................ | 128/864 |

Primary Examiner—Michael A. Brown
Attorney, Agent, or Firm—Richard E. Brink

[57] ABSTRACT

A composite reusable sound attenuating or transmitting device, especially an ear plug, is formed from a core, about which is adhered a strip of slow recovery foam. After each use of the device, the strip of foam is generally removed and discarded; typically, a new strip is applied the next time the device is used.

12 Claims, 2 Drawing Sheets

SEALING STRIP FOR EAR PLUGS AND THE LIKE

BACKGROUND OF THE INVENTION

This invention relates to the sealing of sound transmission or blocking devices to a user's ear canal and is particularly concerned with a means for insuring that ear plugs not only fit snugly and comfortably but also consistently.

Disposable prior art ear plugs are typically made of either soft elastomeric material or resilient foam, which must be inserted deep into the ear canal to be effective. Perhaps the most common ear plug of this type is a die-cut or tapered cylinder of resilient, slow recovery foam about ⅝ inch (16 mm) long, as shown in U.S. Re. Pat. No. 29,487. A somewhat more sophisticated but significantly more expensive product is the "Pod Plug," in which a straight rubbery stiffener extends from a rubbery dish-shaped member and facilitates its insertion into the ear canal; cf. U.S. Pat. No. 5,188,123. Insertion of either type of plug is complicated by the anatomy of the canal and the fact that the plugs are available in only a few sizes. Since ear plugs are typically used once and then thrown away, it is generally impractical to have them custom made to fit each person. Further, even if reusable, custom made ear plugs are expensive.

BRIEF SUMMARY

The present invention provides an inexpensive and simple way to provide devices for transmitting or blocking sound, either completely or selectively, with a consistent and effective seal to the ear canal in which they are inserted. In accordance with the invention predetermined shapes of ear plug cores are provided, each representing a population of similarly shaped ear canals and smaller than the population of ear canals into which it is to be inserted. A strip of adhesive-coated resilient foam is then wrapped around the core to form a complete annular ring that seals to the walls of the ear canal. To simplify the number of strips required, the circumference of the cores at the sealing location will be the same for all cores. After the ear plug has been used and become soiled, the strip of foam is removed and discarded; the next time the ear plug is used, a fresh strip of foam is applied. The strips of foam are simple and cost far less than replacing an entire ear plug.

BRIEF DESCRIPTION OF THE DRAWING

Understanding of the invention will be enhanced by referring to the accompanying drawing, in which like numbers refer to like parts in the several views, and in which.

DETAILED DESCRIPTION

Figure 1:
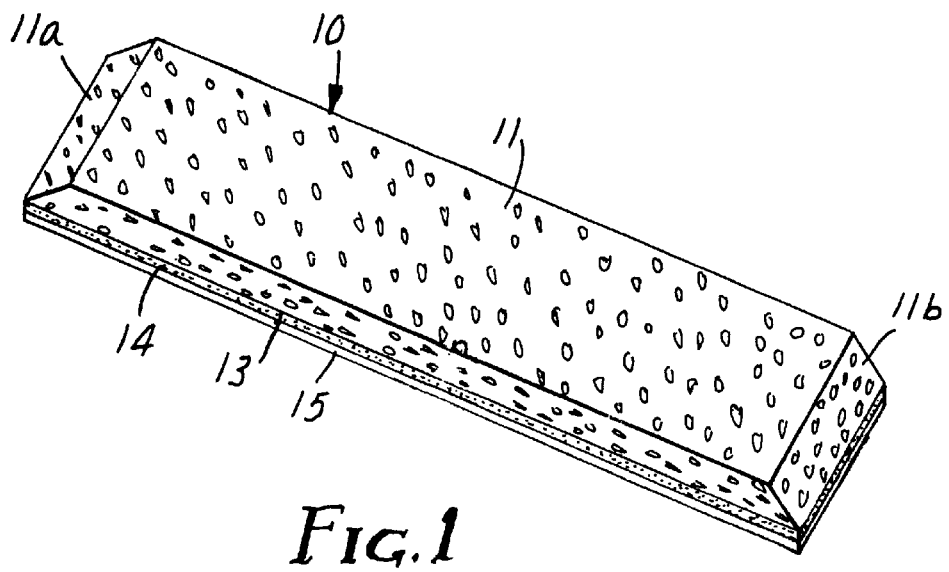
FIG. 1 is a perspective view of a sealing strip in accordance with the invention, showing a generally trapezoidal lateral profile.
Figure 2:
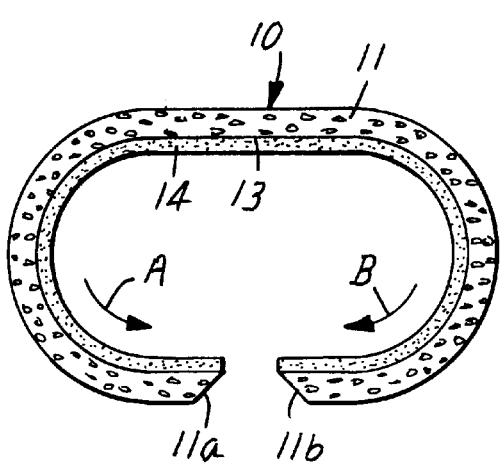
FIG. 2 shows the sealing strip of FIG. 1 being formed into a more or less circular configuration by moving the ends in the directions indicated by arrows A–B.
Figure 3:
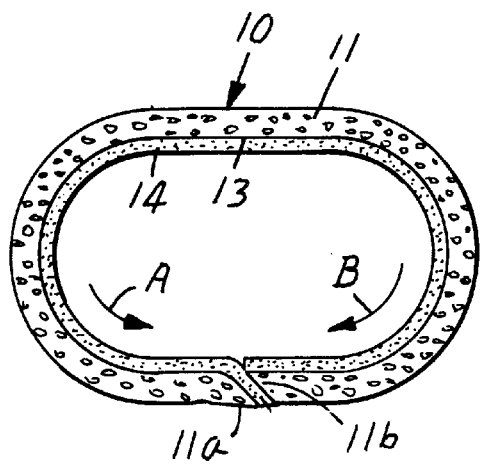
FIG. 3 is similar to FIG. 2, but shows the ends of the sealing strip juxtaposed and adhered together to form a smooth splice when wrapped around an ear plug core (not shown)
Figure 4:
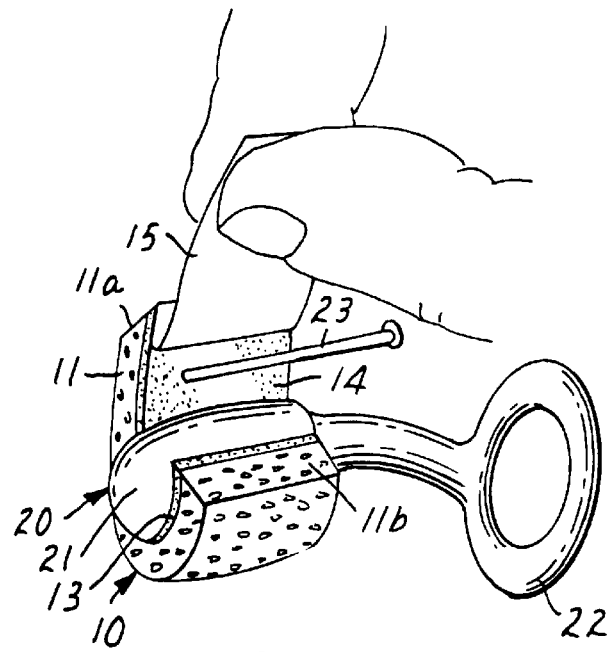
FIG. 4 shows the manner in which the sealing strip is adhered to the periphery of an ear plug core.

As is shown in FIGS. 1–4. sealing strip 10, having tapered end portions 11a and 11b, includes resilient foam layer 11, to surface 13 of which is applied a layer of normally tacky and pressure-sensitive adhesive 14, temporarily protected by liner 15. It is believed that the ends of strip 10 can be tapered by means of a rotary saw or a saw having reciprocating blades, oriented at the proper angle. As is shown in FIG. 4, liner 15 is gradually peeled away as adhesive 14 bonds sealing strip 10 to the periphery of ear plug core 20. It is interesting to note that when liner 15 has been completely removed, end portion 11a of sealing strip 10 will overlap and adhere to end portion 11b, as is shown more particularly in FIG. 3.

Layer 11 is preferably formed of retarded recovery foam, so that a person can squeeze the foam to compress it and thus facilitate inserting the composite ear plug into his or her ear canal. Aided by the warmth of the human body, the foam then gradually expands to conform snugly to the ear canal and effectively attenuate sound. Core 20, which is desirably somewhat flexible, comprises body portion 21, which is to be inserted into a user's ear canal after being wrapped with foam layer 11, and handle 22, which provides a means for grasping during the insertion or removal of the composite ear plug. As a precautionary measure, rip cord 23 may be bonded to sealing strip 10, providing an auxiliary means to help extract strip 10 in the unlikely event that it becomes separated from body portion 21 when core 20 is removed from the user's ear. It will be noted that rip cord 23 operates in a shear mode during extraction of strip 10 from the ear. Rip cord 23 also assists in removal of strip 10 from core 20; in this operation, it is doubled back on itself and functions in a peel mode.

Figure 5:
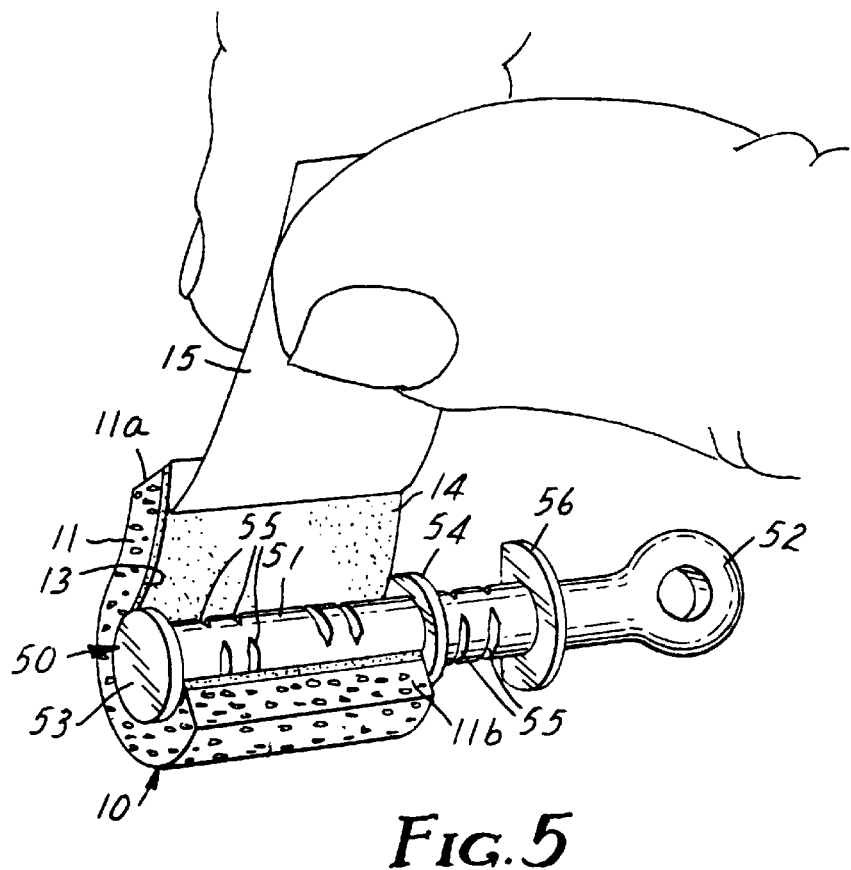
FIG. 5 is similar to FIG. 4 but shows the use of a different type of ear plug core.

FIG. 5 depicts a somewhat more sophisticated type of ear plug core 50, comprising body 51 and handle 52, corresponding to body 21 and handle 22 of core 20. The body 51 of core 50, however, is provided with distal collar 53 and proximal collar 54, between which foam layer 11 is positioned. To accommodate the possibility of using foam layers of different widths to control the degree of attenuation, proximal collar 54 may be eliminated. The use of one or more collars helps to hold layer 11 in place when the composite ear plug is being inserted into or removed from the user's ear canal. The axial cross-section of body 51 is oval, corresponding to the oval cross-section of human ear canals. Body 51 is also provided with several notches 55, imparting flexibility, which enables it to be more easily inserted around the curves of the ear canal. In order to make certain that the composite ear plug is inserted to a consistent depth and a specific location in the ear canal (preferably just beyond the first bend in the canal), core 50 may be provided with asymmetric flange 56, which seats in the concha of the user's ear. Because handle 52 is essentially flat, it is readily gripped between a user's thumb and forefinger, intuitively orienting the oval plug with the oval ear canal. Flange 56, which, as previously noted, is asymmetric, extends only to the rear, thereby avoiding contact with the tragus (the fleshy prominence at the forward portion of the external ear) and insuring that the plug is inserted right way up. The hole in handle 52 provides a convenient way of using a string or chain to link a left and right pair of ear plugs prior to use.

It is contemplated that a set of ear plug cores 20, 50 will be provided, consistent with several ear canal geometries, and that a set of sealing strips having constant length but different thicknesses will also be provided. Each user will first determine the ear plug core that most closely matches the configuration of his or her ear canal and then determine the size of sealing strip that combines comfort and effective sound attenuation. After use, the sealing strip will be removed and discarded, to be replaced by a sealing strip of the same size the next time the user requires ear plugs. By providing sealing strips 10 of different widths, while inserting the composite ear plug to a consistent depth in the ear canal, the degree of sound attenuation can be varied to suit particular requirements. The length of sealing strip 10 will, of course, be appropriate to fit the circumference of body 21 or 51. It has been found that the thickness of foam layer 11 will usually be in the approximate range of $\frac{1}{16}$ inch (1.6 mm) to $\frac{1}{4}$ inch (6.3 mm), typically $\frac{1}{8}$ inch (3.2 mm). Although this invention has been described with particular emphasis on sound-attenuating devices, it will be evident that sound transmission devices such as telephone receivers, stethoscopes, ear phones, hearing aids, etc., could be similarly modified to take advantage of the concept of utilizing a core that is hollow and somewhat smaller than the human ear canal with an appropriately sized strip of replaceable slow recovery foam wrapped around it and temporarily adhered in place to provide effective sealing.

It will also be apparent to those skilled in the art that numerous variations of the foregoing disclosure can be made without departing from the spirit of the invention. For example, it may not be necessary to apply pressure-sensitive adhesive along the entire area of foam strip 11 to obtain adequate adhesion to core 20, 50. Similarly, one edge of strip 11 could be slit or serrated to better enable it to conform to an irregularly shaped core body.

What is claimed is as follows:

1. A composite sound transmitting or attenuating device designed to be inserted into a human ear canal, comprising in combination a core corresponding to the configuration of, but having an axial cross-section that is smaller than that of, the ear canal into which it is to be inserted, and a strip of slow recovery foam wrapped around said core and temporarily adhered thereto, so that, after use, the foam strip can be removed and replaced with a fresh strip, thereby rendering said device reusable.

2. The device of claim 1, wherein the core is flexible and the foam is adhered thereto with a normally tacky and pressure-sensitive adhesive.

3. The device of claim 2, wherein the axial cross-section of the core is oval, corresponding to the cross-section of the human ear canal.

4. The invention of claim 3 wherein the device is a sound-attenuating ear plug, the core body being provided with distal and proximal collars, between which the foam strip is mounted, and the core body also being provided with notches at right angles to the core axis to impart flexibility and facilitate insertion around the bends of a human ear canal.

5. The invention of claim 1 wherein the device is a sound-attenuating ear plug.

6. The ear plug of claim 5 wherein the core is provided with a handle to facilitate insertion and removal.

7. The ear plug of claim 5 wherein the strip of foam is provided with a rip cord as an aid to removal after use.

8. The ear plug of claim 5 wherein the core body is provided with at least a distal collar, against which the foam strip is mounted.

9. The ear plug of claim 8 wherein the core body is provided with both distal and proximal collars, between which the foam strip is mounted.

10. The ear plug of claim 5 wherein the core body is provided with notches at right angles to the core axis to impart flexibility and facilitate insertion around the bends of a human ear canal.

11. The invention of claim 9 wherein the body is provided with an asymmetric flange at the end adjacent the handle to aid in orienting the plug with a human ear canal and provide a consistent depth of insertion.

12. A foam strip having particular utility in fabricating the composite device of claim 1, said strip having first and second faces of unequal length and the ends of said strip being tapered, so as to present a trapezoidal lateral profile, the longer face of said strip being coated with a normally tacky and pressure-sensitive adhesive.

* * * * *